US 8,055,035 B2

(12) United States Patent
Okugawa et al.

(10) Patent No.: US 8,055,035 B2
(45) Date of Patent: Nov. 8, 2011

(54) SPECTRAL IMAGE PROCESSING METHOD, COMPUTER-EXECUTABLE SPECTRAL IMAGE PROCESSING PROGRAM, AND SPECTRAL IMAGING SYSTEM

(75) Inventors: Hisashi Okugawa, Yokosuka (JP); Masafumi Mimura, Aseo (JP)

(73) Assignee: Nikon Corporation, Tokyo (JP)

( * ) Notice: Subject to any disclaimer, the term of this patent is extended or adjusted under 35 U.S.C. 154(b) by 1042 days.

(21) Appl. No.: 11/913,281

(22) PCT Filed: Feb. 1, 2007

(86) PCT No.: PCT/JP2007/051698
§ 371 (c)(1),
(2), (4) Date: Oct. 31, 2007

(87) PCT Pub. No.: WO2007/097170
PCT Pub. Date: Aug. 30, 2007

(65) Prior Publication Data
US 2009/0080722 A1    Mar. 26, 2009

(30) Foreign Application Priority Data
Feb. 23, 2006 (JP) ................ 2006-046508

(51) Int. Cl.
*G06K 9/00* (2006.01)
(52) U.S. Cl. ........ 382/128; 382/236; 382/115; 382/118; 345/581; 345/589
(58) Field of Classification Search .......... 382/128, 382/133, 190, 276, 235, 243, 277; 702/22, 702/27, 30; 356/317, 318, 417, 326, 328
See application file for complete search history.

(56) References Cited

U.S. PATENT DOCUMENTS

| 5,798,262 | A | 8/1998 | Garini et al. |
| 5,991,456 | A | 11/1999 | Rahman et al. |
| 6,015,667 | A | 1/2000 | Sharaf |
| 6,341,257 | B1 * | 1/2002 | Haaland ............ 702/27 |
| 6,415,233 | B1 | 7/2002 | Haaland |
| 6,750,964 | B2 | 6/2004 | Levenson et al. |
| 6,763,308 | B2 * | 7/2004 | Chu et al. ............ 702/19 |

(Continued)

FOREIGN PATENT DOCUMENTS

JP    11-185036 A    7/1999

(Continued)

OTHER PUBLICATIONS

Zimmermann et al., "Spectral imaging and its applications in live cell microscopy," FEBS Letters 546, 2003, pp. 87-92.

(Continued)

*Primary Examiner* — Vikkram Bali
*Assistant Examiner* — Nancy Bitar
(74) *Attorney, Agent, or Firm* — Miles & Stockbridge P.C.

(57) ABSTRACT

A spectral image processing method is capable of reducing noise while maintaining necessary information. The spectral image processing method performs processing on a spectral image of a specimen, including a step of normalizing spectra (=spectral brightness curves) of respective pixels constituting the spectral image such that their brightness levels become equal, a step of smoothing the normalized spectra in spatial directions of the respective pixels, and a step of denormalization of multiplying spectra of the respective pixels obtained by the smoothing by either one of brightness levels of the pixels corresponding the spectra and values corresponding to the brightness levels. Consequently, the noise can be reduced while information on brightness distribution on the image is maintained.

15 Claims, 7 Drawing Sheets

U.S. PATENT DOCUMENTS

| | | | |
|---|---|---|---|
| 6,888,963 B2 * | 5/2005 | Nichogi | 382/167 |
| 6,894,699 B2 * | 5/2005 | Someya et al. | 345/611 |
| 6,906,859 B2 | 6/2005 | Nihoshi et al. | |
| 7,129,959 B2 | 10/2006 | Someya et al. | |
| 7,283,684 B1 | 10/2007 | Keenan | |
| 7,321,791 B2 | 1/2008 | Levenson et al. | |
| 7,420,674 B2 | 9/2008 | Gerstner et al. | |
| 7,457,472 B2 * | 11/2008 | Pace et al. | 382/236 |
| 7,471,831 B2 * | 12/2008 | Bearman et al. | 382/191 |
| 7,555,155 B2 | 6/2009 | Levenson et al. | |
| 2002/0047907 A1 | 4/2002 | Chen et al. | |
| 2002/0090630 A1 | 7/2002 | Hazama | |
| 2005/0111017 A1 * | 5/2005 | Takahashi et al. | 358/1.9 |
| 2006/0108540 A1 | 5/2006 | Nakajima | |
| 2006/0119896 A1 * | 6/2006 | Chen et al. | 358/3.26 |
| 2007/0099535 A1 * | 5/2007 | Riebersal et al. | 446/46 |
| 2009/0080722 A1 | 3/2009 | Okugawa et al. | |

FOREIGN PATENT DOCUMENTS

| | | |
|---|---|---|
| JP | 2000-503774 A | 3/2000 |
| JP | 2000-511315 A | 8/2000 |
| JP | 2002-44570 A | 2/2002 |
| JP | 2002-152762 A | 5/2002 |
| JP | 2002-168868 A | 6/2002 |
| JP | 3351536 B2 | 9/2002 |
| JP | 2003-083894 A | 3/2003 |
| JP | 2004-163312 A | 6/2004 |
| WO | WO 2005/013622 A1 | 2/2005 |
| WO | WO 2005/036143 A1 | 4/2005 |

OTHER PUBLICATIONS

Dickinson et al., "Mulit-Spectral Imaging and Linear Unmixing Add a Whole New Dimension to Laser Scanning Fluorescence Microscopy", BioTechniques, vol. 31, No. 6, 2001, pp. 1272, 1274-1276, 1278.

* cited by examiner

[Fig. 1]
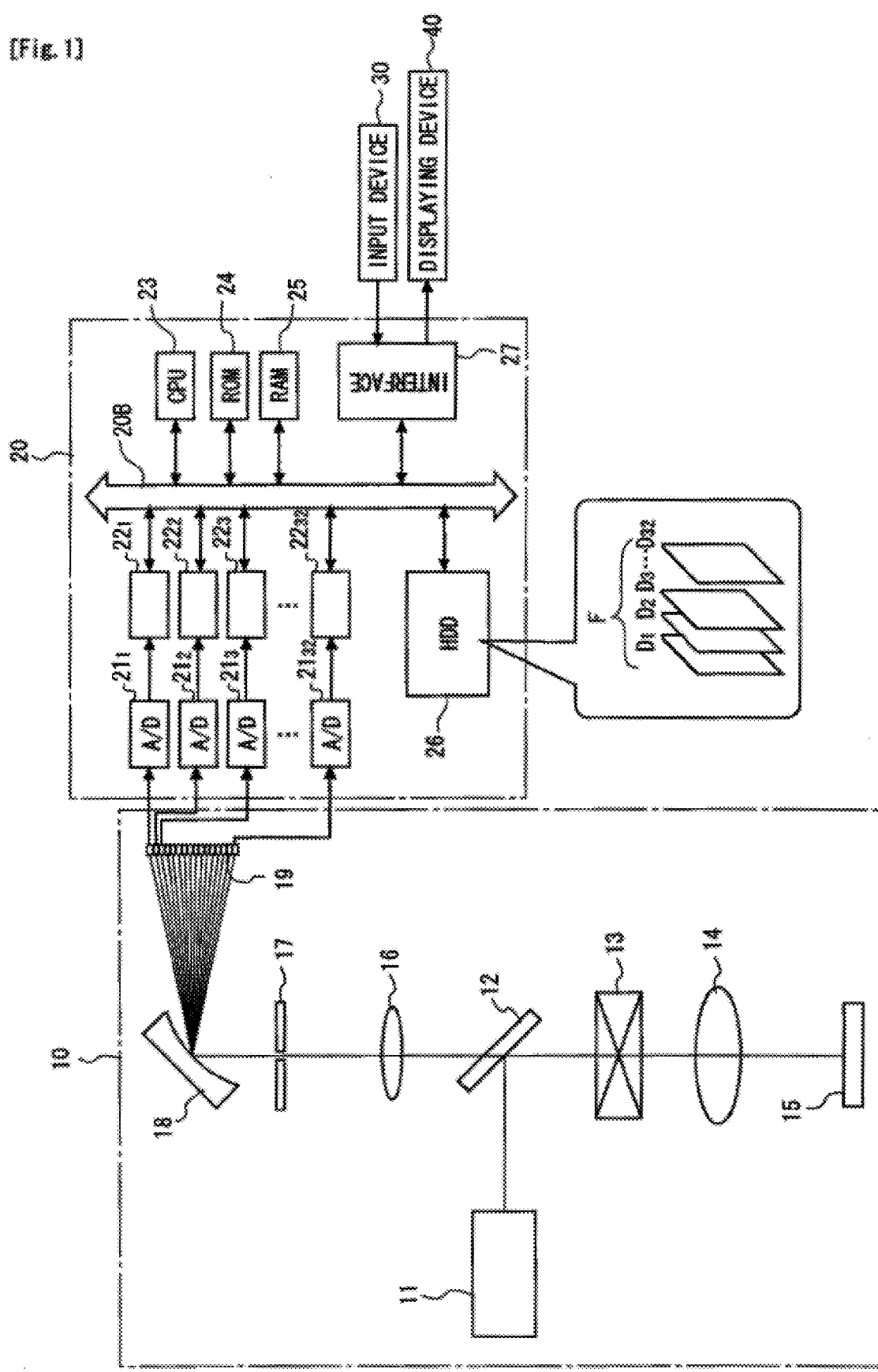

[Fig. 2]
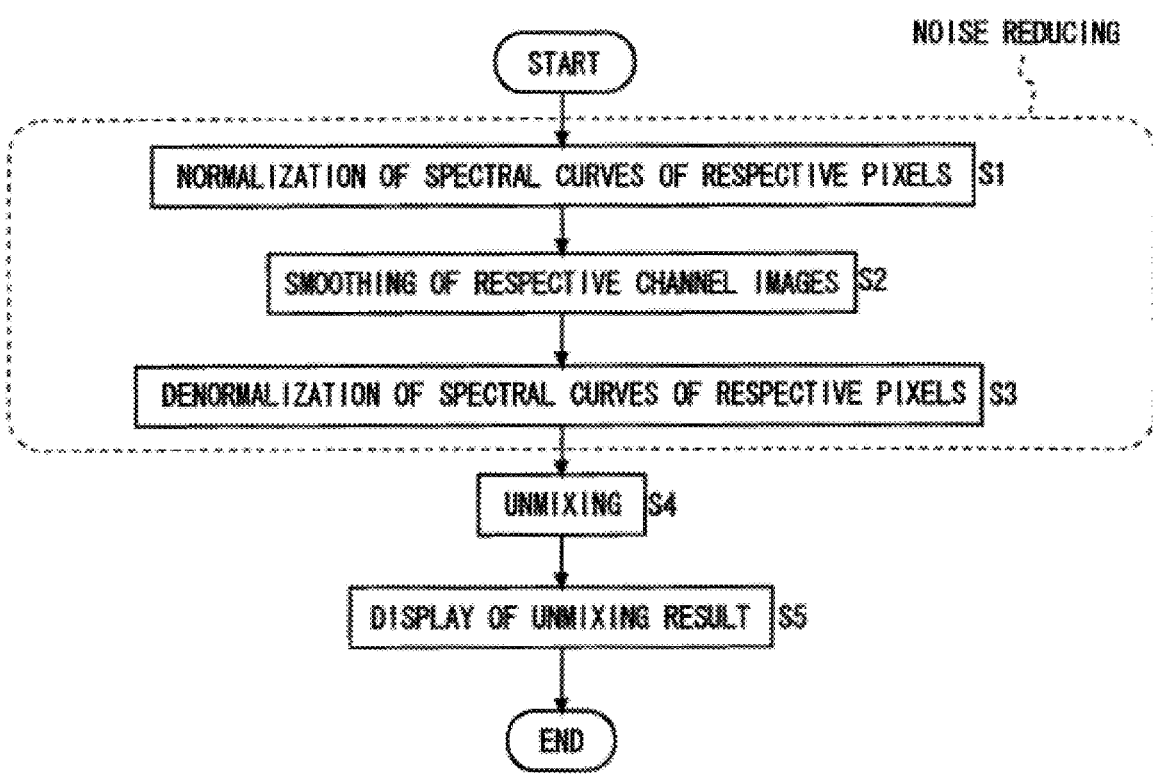

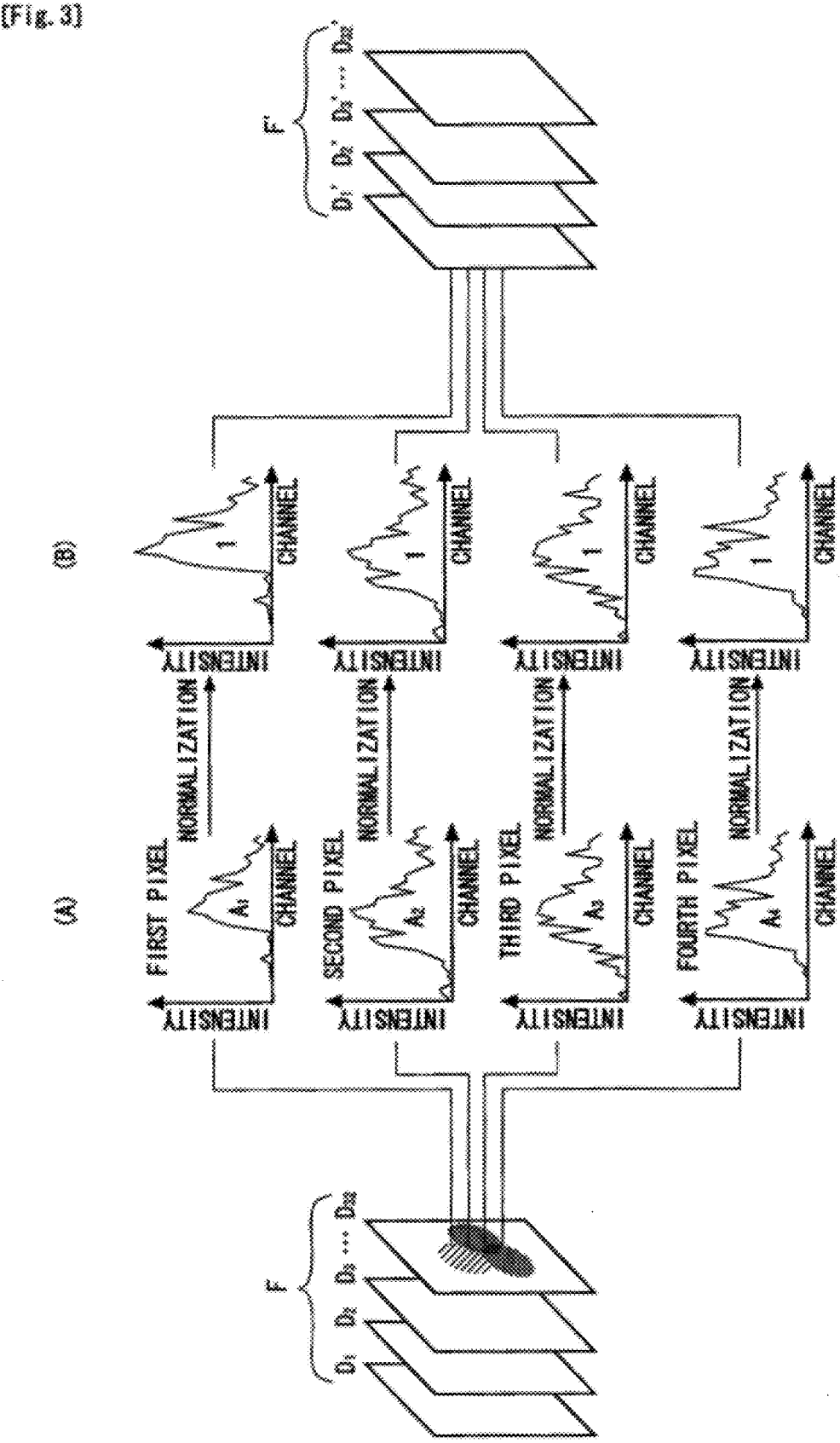
[Fig. 3]

[Fig. 4]
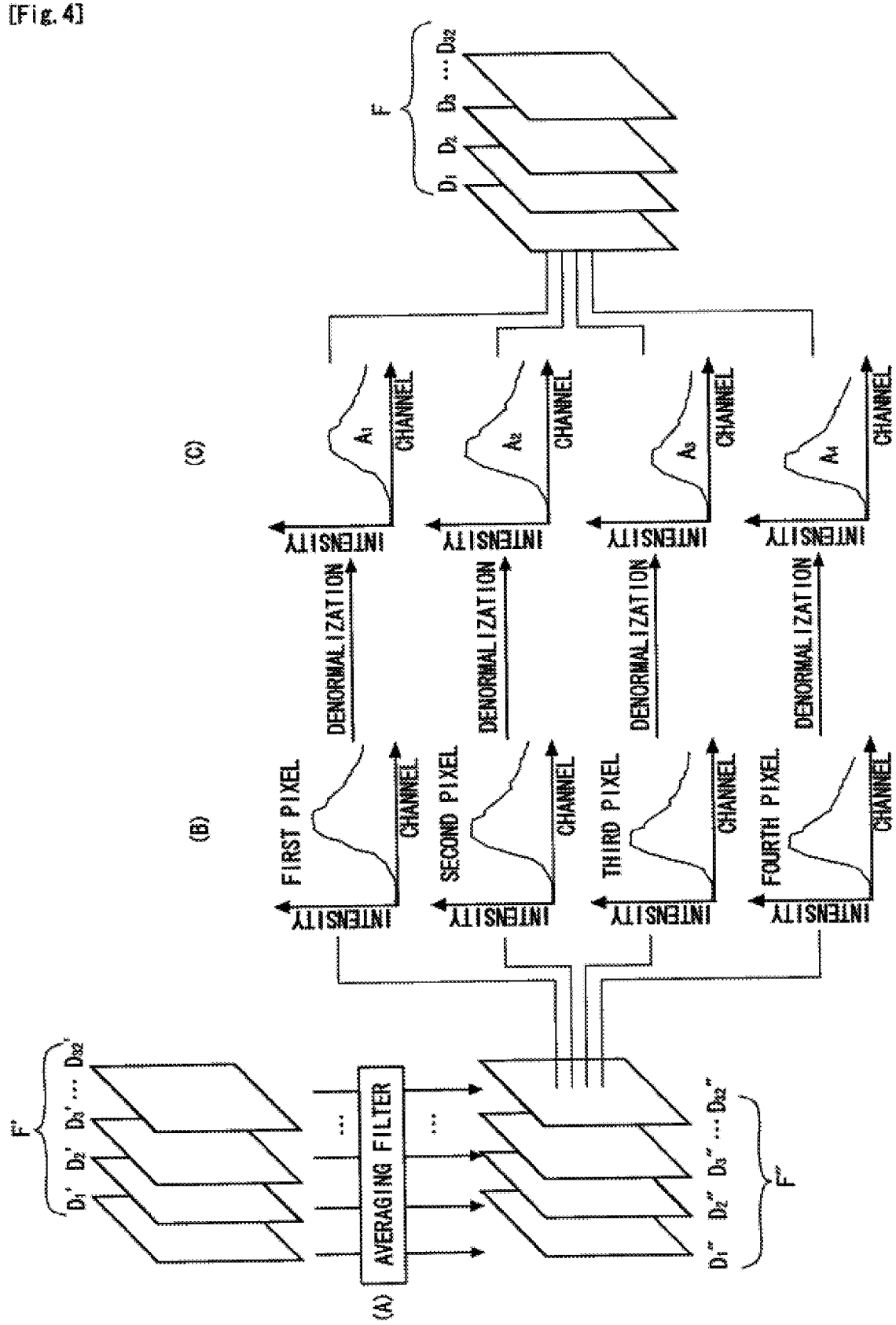

[Fig. 5]
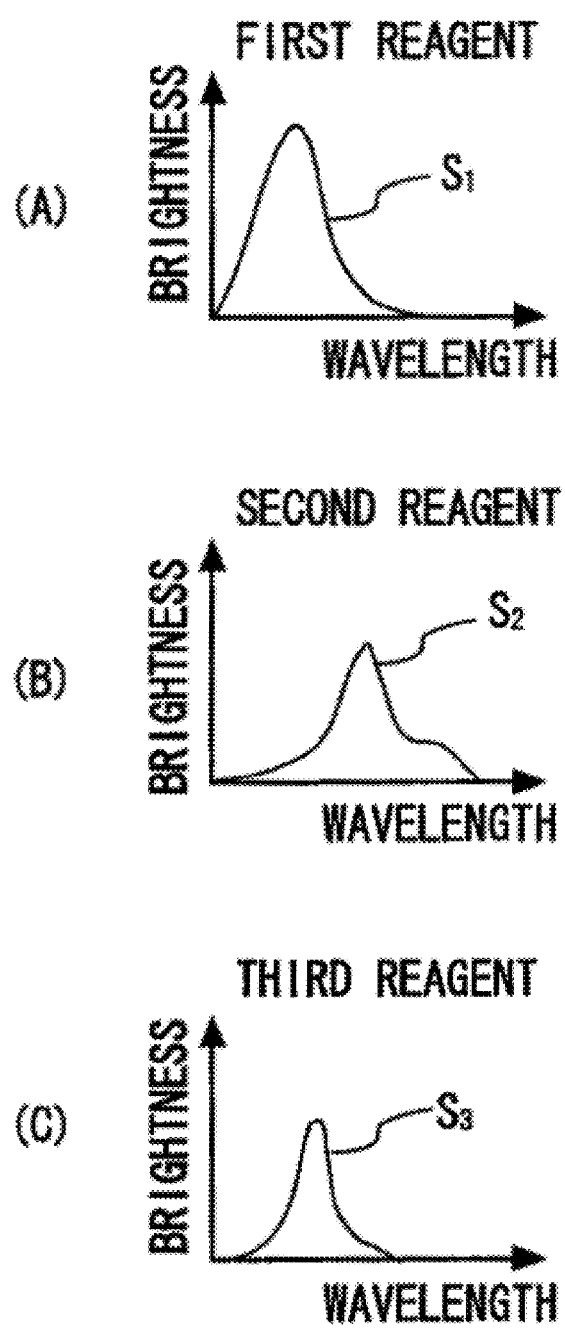

[Fig. 6]
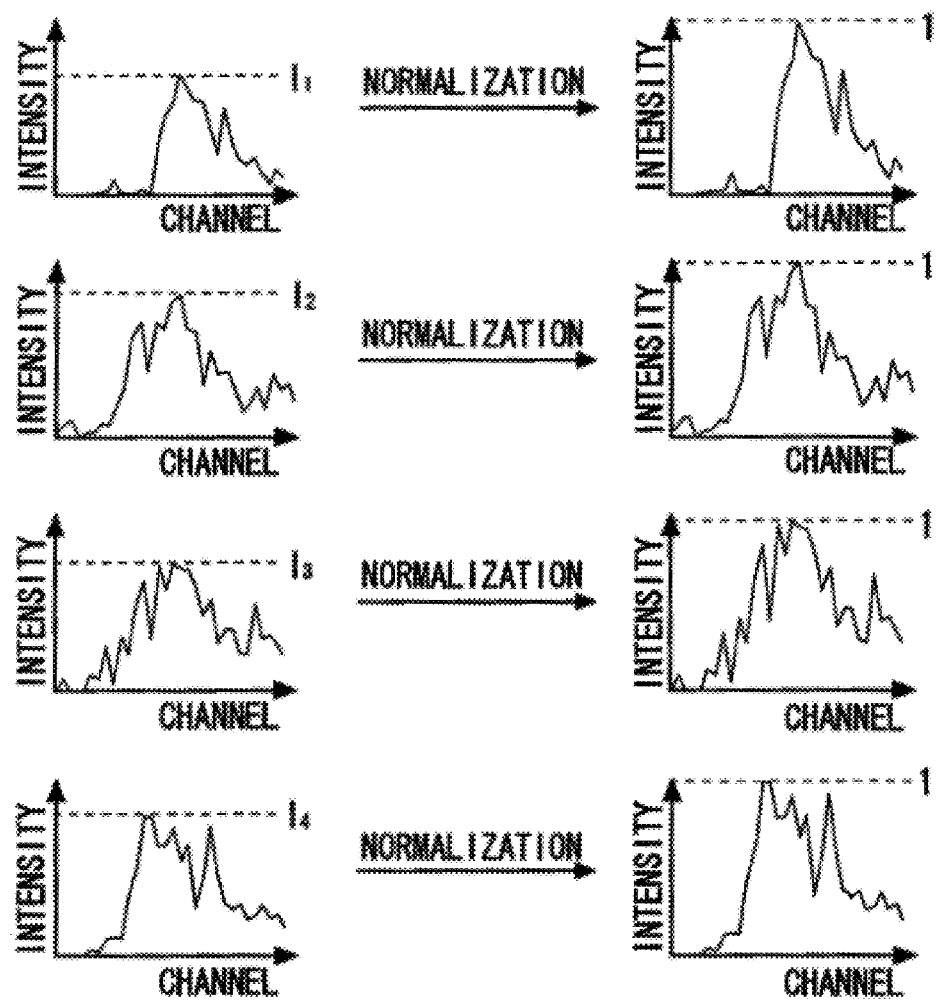

[Fig. 7]
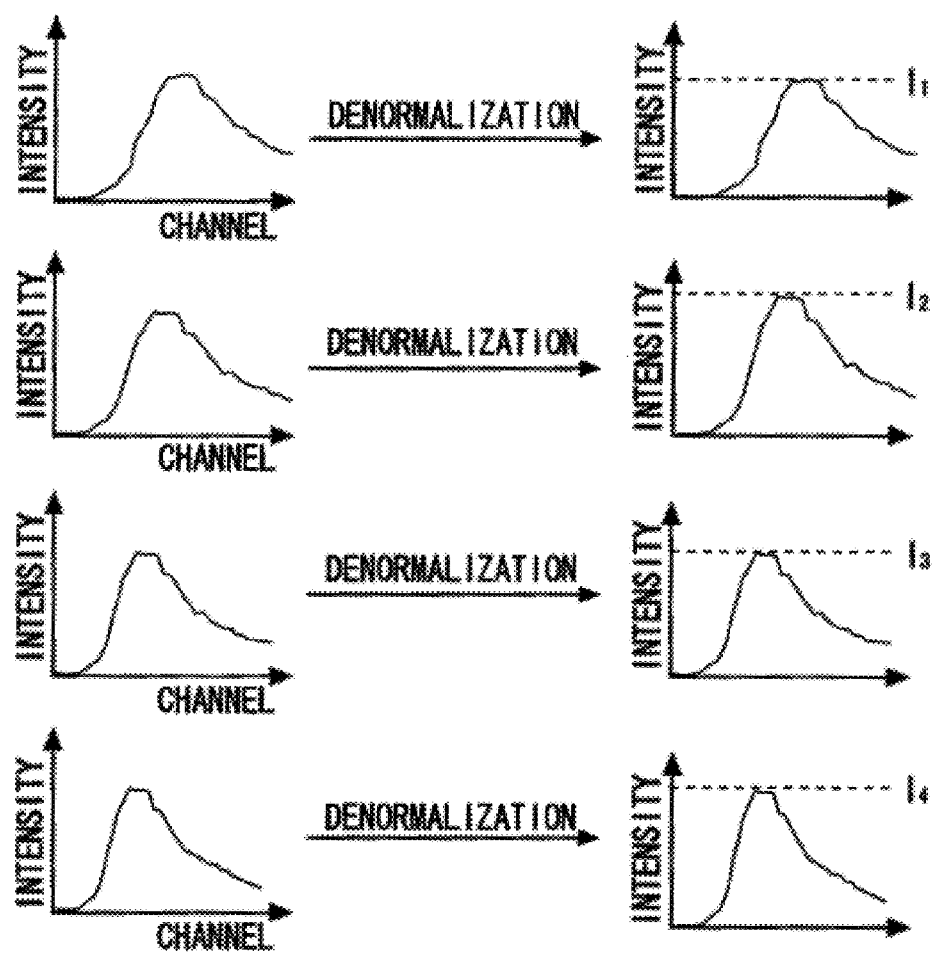

SPECTRAL IMAGE PROCESSING METHOD, COMPUTER-EXECUTABLE SPECTRAL IMAGE PROCESSING PROGRAM, AND SPECTRAL IMAGING SYSTEM

CROSS-REFERENCE TO RELATED APPLICATION

This application is a 371 of International Application Number PCT/JP2007/051698, filed Feb. 1, 2007, which claims the priority of Japanese Patent Application Number 2006-046508 filed Feb. 23, 2006.

TECHNICAL HELD

The present invention relates to a spectral image processing method of processing a spectral image acquired by a microscope or the like and a computer-executable spectral image processing program. Further, the present invention relates to a spectral imaging system such as a spectral-imaging fluorescent laser microscope.

BACKGROUND ART

In dynamic observation of an organism cell, a sample is labeled by a fluorescent material such as a fluorescent reagent or a fluorescent protein and observed by an optical microscope such as a fluorescent laser microscope in some cases. When plural fluorescent materials are used simultaneously, it is necessary to detect images of respective wavelength components (a spectral image).

However, when emission wavelengths of the plural fluorescent materials overlap, the images of these respective materials cannot be separated by the optical microscope, so that an analysis method of importing the spectral image detected by the microscope into a computer and separating (unmixing) it into the images of the respective materials becomes effective (see Non-Patent Document 1 or the like). Incidentally, in this unmixing, emission spectral data of the respective materials disclosed by manufacturers of reagents and the like is used.

Non-Patent Document 1: Timo Zimmermann, JensRietdorf, Rainer Pepperkok, "Spectral imaging and its applications in live cell microscopy", FEBS Letters 546 (2003), P 87-P 92, 16 May 2003

DISCLOSURE

Problems to be Solved

However, measurement noise is superimposed on a spectral image being actual measurement data due to instability of a light source of a microscope, electric noise of a light detecting element of the microscope, and so on, which exerts a strong influence on the accuracy of unmixing. In particular, when spectra of plural fluorescent reagents are similar, for example, when peak wavelengths are close to each other, the accuracy of unmixing becomes worse if the measurement noise is large.

Among measures against this is a method of smoothing adjacent images by performing spatial filter processing, for example, averaging filter processing or median-filter processing, which is effective as a method of reducing noise. However, in such a method, brightnesses are also averaged, which causes a problem that spatial resolution is deteriorated and on a simple average, the influence of a pixel with a high brightness increases, so that the noise reduction is not necessarily sufficient.

Hence, an object of the present invention is to provide a spectral image processing method capable of reducing noise without damaging necessary information as much as possible and a computer-executable spectral image processing program. Further, an object of the present invention is to provide a high-performance spectral imaging system.

Means for Solving the Problems

A spectral image processing method of the present invention is a spectral image processing method of performing processing on a spectral image of a specimen, including: a step of normalizing spectra (=spectral brightness curves) of respective pixels constituting the spectral image such that their brightness levels become equal; a step of smoothing the normalized spectra in spatial directions of the respective pixels; and a step of denormalization of multiplying spectra of the respective pixels obtained by the smoothing by either one of brightness levels of the pixels corresponding the spectra and values corresponding to the brightness levels.

Incidentally, the normalization is performed such that brightness integral values of the spectra become equal, and the denormalization is performed such that the brightness integral values of the spectra return to values before the normalization.

Moreover, the normalization is performed such that brightness maximum values of the spectra become equal, and the denormalization is performed such that the brightness maximum values of the spectra return to values before the normalization.

Further, another spectral image processing method of the present invention includes an unmixing step of, based on a spectral image subjected to image processing using any spectral image processing method of the present invention and emission spectral information of plural materials contained in the specimen, separating and finding respective contributions of the plural materials to the spectral image.

Furthermore, a spectral image processing program of the present invention causes a computer to execute any spectral image processing method of the present invention.

Moreover, a spectral imaging system of the present invention includes: a spectral imaging unit which acquires a spectral image of a specimen; and a spectral image processing unit which imports the acquired spectral image and executes any spectral image processing method of the present invention.

Effect

According to the present invention, a spectral image processing method capable of reducing noise without damaging necessary information as much as possible and a computer-executable spectral image processing program are realized. Further, according to the present invention, a high-performance spectral imaging system is realized.

BRIEF DESCRIPTION OF THE DRAWINGS

FIG. 1 is a configuration diagram of a system of an embodiment;

FIG. 2 is an operational flowchart of a CPU 23;

FIG. 3 is a diagram explaining normalizing processing;

FIG. 4 is a diagram explaining smoothing processing and denormalizing processing;

FIG. 5 is a diagram showing examples of emission spectral curves $S_1$, $S_2$, $S_3$ of fluorescent reagents;

FIG. 6 is a diagram showing changes of spectral curves when the standard of normalization is set to a brightness maximum value; and FIG. 7 is a diagram showing changes of the spectral curves when the standard of denormalization is set to the brightness maximum value.

DETAILED DESCRIPTION OF THE EMBODIMENTS

An embodiment of the present invention will be described. This embodiment is an embodiment of a spectral imaging fluorescent confocal laser microscope system.

First, the configuration of this system will be described.

FIG. 1 is a configuration diagram of this system. As shown in FIG. 1, this system includes a main body of a microscope 10, a computer 20 connected thereto, and an input device 30 and a displaying device 40 connected thereto. The input device 30 is a mouse, a keyboard, and so on, and the displaying device 40 is an LCD or the like.

In the main body 10, a laser light source 11, a dichroic mirror 12, an optical scanner 13, an objective lens 14, a sample 15, an observation lens 16, a pinhole mask 17, a spectroscopic element 18, and a multichannel light detector 19 are placed. The sample 15 is labeled by plural types (for example, three types) of fluorescent reagents, and the multichannel light detector 19 has many (for example, 32) wavelength channels.

The computer 20 includes a CPU 23, a ROM 24 into which a basic operation program of the CPU 23 is written, a RAM 25 used as a temporary storage means while the CPU 23 is operating, a hard disk drive 26 to save information for a long time. an interface circuit 27 interfacing the input device 30 and the displaying device 40, A/D converting circuits $21_1$, $21_2$, ..., $21_{32}$ of the same number as wavelength channels of the multichannel light detector 19, and frame memories $22_1$, $22_2$ ..., $22_{32}$ of the same number as the A/D converting circuits. The frame memories $22_1$, $22_2$, ..., $22_{32}$, the hard disk drive 26, the CPU 23, the ROM 24, the RAM 25, the interface circuit 27 are connected via a bus 20B. An operation program of the CPU 23 necessary for this system is previously stored in the hard disk drive 26.

Laser light (for example, having a wavelength of 488 nm) is emitted from the laser light source 11 of the main body of the microscope 10. This laser light is reflected by the dichroic mirror 12 and collected at a point on the sample 15 via the optical scanner 13 and the objective lens 14 in order. At the light collecting point, fluorescence (for example, having a wavelength of 510 nm to 550 nm) is generated, and when entering the dichroic mirror 12 via the objective lens 14 and the optical scanner 13 in order, the fluorescence is transmitted through this dichroic mirror 12 and enters the pinhole mask 17 via the observation lens 16. This pinhole mask 17 forms a conjugate relation with the sample 15 by the observation lens 16 and the objective lens 14 and has a function of letting only a necessary ray of light of the fluorescence generated on the sample 15 pass therethrough. As a result, a confocal effect of the main body of the microscope 10 can be obtained. When entering the spectroscopic element 8, the fluorescence which has passed through the pinhole mask 17 is separated into plural wavelength components. These respective wavelength components enter wavelength channels different from each other of the multichannel light detector 19 and detected independently and simultaneously.

The respective wavelength channels (here, 32 wavelength channels) of the multichannel light detector 19 detect, for example, 32 kinds of wavelength components different in steps of 5 nm in a wavelength range from 510 nm to 550 nm. Respective signals outputted from the 32 wavelength channels are imported in parallel into the computer 20 and individually inputted to the frame memories $22_1$, $22_2$, ..., $22_{32}$ via the A/D converting circuits $21_1$, $21_2$, ..., $21_{32}$.

This multichannel light detector 19 and the optical scanner 13 are synchronously driven, and thereby the signals are repeatedly outputted from the multichannel light detector 19 during a period of two-dimensional scanning at the light collecting point on the sample 15. At this time, images of the respective wavelength channels of the sample 15 are gradually accumulated in the frame memories $22_1$, $22_2$, ..., $22_{32}$. The images (channels images $D_1$, $D_2$, ..., $D_{32d}$) of the respective wavelength channels accumulated in the frame memories $22_1$, $22_2$, ..., $22_{32}$ are read in an appropriate timing by the CPU 23, integrated into one spectral image F, and then stored in the hard disk drive 26.

Incidentally, in the hard disk drive 26 of the computer 20, in addition to this spectral image F, emission spectral data of the fluorescent reagents used for the sample 15 is previously stored. This emission spectral data is disclosed by manufactures of the fluorescent reagents or the like and loaded into the computer 20, for example, by the Internet, a storage medium, or the like.

Next, the operation of the CPU 23 after the spectral image F is acquired will be described.

FIG. 2 is an operational flowchart of the CPU 23. As shown in FIG. 2, after executing noise reducing processing constituted by normalizing processing (step S1), smoothing processing (step S2), and denormalizing processing (step S3), the CPU 23 executes unmixing processing (step S4), and displaying processing (step S5). These steps will be described below step by step.

Normalizing Processing (step S1):

In this step, first, as shown in FIG. 3(A), the CPU 23 refers to spectral curves of respective pixels from the spectral image F. In FIG. 3(A), only spectral curves of some four pixels (a first pixel, second pixel, third pixel, fourth pixel) are shown. The horizontal axis of the spectral curve is a wavelength channel, and the vertical axis thereof is a brightness value.

Brightness levels of the spectral curves of the respective pixels vary as shown in FIG. 3(A). A brightness integral value $A_1$ of the spectral curve of the first pixel indicates a total brightness of the first pixel, a brightness integral value $A_2$ of the spectral curve of the second pixel indicates a total brightness of the second pixel, a brightness integral value $A_3$ of the spectral curve of the third pixel indicates a total brightness of the third pixel, and a brightness integral value $A_4$ of the spectral curve of the fourth pixel indicates a total brightness of the fourth pixel.

Further, as shown in FIG. 3(A), shapes of the spectral curves vary among the respective pixels. Between close pixels, there is a high possibility that rough shapes of the spectral curves are similar, but fine shapes of the spectral curves differ from each other even if the pixels are close since random measurement noise is superimposed.

Then, as shown in FIG. 3(B), the CPU 23 normalizes the spectral curves of the respective pixels such that their brightness integral values A become one. In the normalization of each spectral curve, it is only required to multiply brightness values of the respective wavelength channels of the spectral curve by a normalizing coefficient=(1/current brightness integral value).

When a spectral image F' constituted by the normalized spectral curves is referred to here as shown at the right side of FIG. 3, any of the total brightnesses of the respective pixels becomes one in the spectral image F'. That is to say, brightness information of the spectral curves of the respective pixels is excluded from the spectral image F', and only shape information of the spectral curves of the respective pixels is maintained. Hereinafter, respective wavelength components (channel images) of this spectral image F' are represented as $D_1', D_2', \ldots, D_{32}'$.

Smoothing Processing (step S2):

In this step, as shown in FIG. 4(A), the CPU 23 performs averaging filter processing on each of the above channel images $D_1', D_2', \ldots, D_{32}'$. Therefore, each of the channel images $D_1', D_2', \ldots, D_{32}'$ is smoothed in a spatial direction.

In the averaging filter processing for the channel image D', a mask (which is a computational mask), for example, having an opening of three pixels high by three pixels wide is used. This mask is put into the channel image D', and the brightness value of a target pixel located at the center of the opening of the mask is replaced with a brightness mean value of all the pixels in the opening. By repeatedly performing this processing while shifting a mask position on the channel image D', processing of the whole area of the image is completed.

Here, if the respective channel images after the smoothing are represented as $D_1'', D_2'', \ldots, D_{32}''$ as shown in the lower left of FIG. 4 and a spectral image F''' constituted by these channel images $D_1'', D_2'', \ldots, D_{32}''$ is referred to, in the spectral image F''', as shown in FIG. 4(B), shapes of the spectral curves of the respective pixels become smooth. This is because the shapes of the spectral curves of the respective pixels are influenced by the shapes of the spectral curves of their adjacent pixels by the smoothing. This indicates that noise is removed from the shape information of the spectral curves of the respective pixels.

Denormalizing Processing (step S3):

In this step, as shown in FIG. 4(C), the CPU 23 denormalizes the spectral curves of the respective pixels constituting the spectral image F''' such that their brightness integral values return to the brightness integral values before the normalization (see FIG. 3(A)). Concerning the spectral curve of the first pixel, it is denormalized such that its brightness integral value returns to the value $A_1$ before the normalization, concerning the spectral curve of the second pixel, it is denormalized such that its brightness integral value returns to the value $A_2$ before the normalization, concerning the spectral curve of the third pixel, it is denormalized such that its brightness integral value returns to the value $A_3$ before the normalization, and concerning the spectral curve of the fourth pixel, it is denormalized such that its brightness integral value returns to the value $A_4$ before the normalization. In the denormalization of each spectral curve, it is only required to multiply brightness values of the respective wavelength channels of the spectral curve by an denormalizing coefficient=(brightness integral value before normalization/current brightness integral value).

A spectral image constituted by the above spectral curves after the denormalization is stored again as the spectral image F in the hard disk drive 26 as shown in the lower right of FIG. 4.

In this spectral image F, the brightness information of the spectral curves of the respective pixels is recovered by the denormalization. Besides, noise is removed from the shape information of the spectral curves of the respective pixels as described above. Accordingly, this spectral image F accurately represents the state of the sample 15.

Unmixing Processing (step S4):

In this step, first, the CPU 23 reads the spectral image F and the emission spectral data of the fluorescent reagents from the hard disk drive 26.

As shown in FIGS. 5(A), (B), (C), the emission spectral data represents emission spectral curves $S_1, S_2, S_3$ of the three types of fluorescent reagents (a first reagent, second reagent, third reagent). These emission spectral curves $S_1, S_2, S_3$ are each represented by a one-dimensional matrix such as shown in equation (1).

[Equation 1]

$$S_1 = \begin{bmatrix} s_{11} \\ s_{21} \\ s_{31} \\ \vdots \\ s_{321} \end{bmatrix}, S_2 = \begin{bmatrix} s_{12} \\ s_{22} \\ s_{32} \\ \vdots \\ s_{322} \end{bmatrix}, S_3 = \begin{bmatrix} s_{13} \\ s_{23} \\ s_{33} \\ \vdots \\ s_{323} \end{bmatrix} \quad (1)$$

Note that an element $S_{ij}$ in equation (1) is a brightness value of an ith wavelength of a jth reagent. The number of elements in a wavelength direction of this matrix is set to 32 to match the data amount in a wavelength direction of the spectral image F (=the number of wavelength channels of the multi-channel light detector 19).

The CPU 23 performs unmixing processing of the spectral image F based on these emission spectral curves $S_1, S_2, S_3$, and the unmixing is performed for each pixel of the spectral image F.

A spectral curve f of some pixel included in the spectral image F is represented by a one-dimensional matrix such as shown in equation (2). An element $f_i$ is a brightness value of an ith wavelength channel of this pixel.

[Equation 2]

[Equation 2]

$$f = \begin{bmatrix} f_1 \\ f_2 \\ f_3 \\ \vdots \\ f_{32} \end{bmatrix} \quad (2)$$

Accordingly, if the contribution ratio of the first reagent to this pixel is taken as $p_1$, the contribution ratio of the second reagent thereto is taken as $p_2$, and the contribution ratio of the third reagent thereto is taken as $p_3$, the spectral curve f of this pixel is represented by equation (3).

[Equation 3]

$$f = S_1 \cdot p_1 + S_2 \cdot p_2 + S_3 \cdot p_3 \quad (3)$$

Further, if the respective emission spectral curves of the three types of fluorescent reagents are brought together and represented by one matrix S as shown in equation (4), and the respective contribution ratios of the three types of fluorescent reagents are brought together and represented by one matrix P as shown in equation (5), equation (3) is transformed as shown in equation (6).

[Equation 4]

$$S = [S_1 \ S_2 \ S_3] \quad (4)$$

[Equation 5]

$$P = \begin{bmatrix} p_1 \\ p_2 \\ p_3 \end{bmatrix} \quad (5)$$

[Equation 6]

$$f = S \cdot P \quad (6)$$

Hence, the CPU 23 can unmix this pixel by assigning information on the spectral curve f of this pixel and information on the emission spectral curve S to equation (6) and solving this equation for the contribution ratio P.

Note, however, that since the number of wavelength channels (here, 32) is set larger than the number of types of fluorescent reagents (here, 3) as described above in this system, the CPU 23 applies a least squares method.

The least squares method is to prepare equation (7) with consideration given to an error a in equation (6) and find the contribution ratio P such that a square value of the error a becomes minimum.

[Equation 7]

$$f = S \cdot P + \epsilon \quad (7)$$

An equation to calculate the contribution ratio P by this least squares method is shown as in equation (8).

[Equation 8]

$$P = (S^T S)^{-1} S^T f \quad (8)$$

Note that $S^T$ is a transposed matrix of S.

Accordingly, the CPU unmixes this pixel by assigning the information on the spectral curve f of this pixel and the information on the emission spectral curve S to this equation (8). Then, the CPU 23 performs this unmixing on all the pixels of the spectral image F, respectively, and completes this step.

As just described, the unmixing processing in this step is performed by the well-known least squares method, but since the spectral image F accurately represents the state of the sample 15 as described above, the accuracy of this unmixing processing is higher than that of the conventional one.

Displaying Processing (step S5):

In this step, the CPU 23 displays the information on the contribution ratios (contribution ratios of the respective fluorescent reagents to the respective pixels) found by the unmixing processing on the displaying device 40. The information on the contribution ratios may be displayed as numeric data, but in order to intuitively inform a user of it, it is desirable that the CPU 23 creates an unmixed image colored according to the contribution ratios and displays it.

As described above, the computer 20 of this system removes noise from the spectral image prior to the unmixing processing, but this noise reducing processing does no damage to the brightness information of the spectral curves of the respective pixels as described above, so that the spectral image F which accurately represents the state of the sample 15 can be obtained. Hence, the accuracy of the unmixing processing by the computer 20, that is, the performance of this system is certainly improved.

Incidentally, in the noise reducing processing (steps S1 to S3) of this system, the standards of the normalization and the denormalization of the spectral curve are set to the brightness integral value of the spectral curve, but may be set to a brightness maximum value or a brightness intermediate value instead of the brightness integral value.

In FIG. 6 and FIG. 7, changes of the spectral curves when the standards of the normalization and the denormalization are set to the brightness maximum value are shown. Referring to FIG. 6 and FIG. 7, it can be seen that peaks of the spectral curves of the respective pixels before the normalization are $I_1$, $I_2$, $I_3$, $I_4$, but all become one after the normalization, and after the denormalization, return to the values $I_1$, $I_2$, $I_3$, $I_4$ before the normalization.

Further, in the smoothing processing (step S2) of this system, the averaging filter processing is applied, but instead of the averaging filter processing, a different spatial filter processing such as weighted averaging filter processing or a median-filter processing may be applied. For reference's sake, the median-filter processing is to find a brightness intermediate value of all the pixels in the opening instead of calculating the brightness mean value thereof. It is desirable that the type of such filter processing be selected appropriately according to the type of the measurement noise generated in the main body of the microscope 10. For reference's sake, the averaging filter processing is effective when nose is generated uniformly on the channel image, and the median-filter processing is effective when noise is generated suddenly on the channel image (salt-and-pepper noise).

Furthermore, in the smoothing processing (step S2) of this system, the size of the mask (size of a filter) is 3 pixels×3 pixels=9 pixels, but may be changed to a different size. It is desirable that this size be selected appropriately according to the type of the measurement noise generated in the main body of the microscope 10.

Moreover, in the noise reducing processing (steps S1 to S3) of this system, the start timing of the smoothing processing is after the normalization of the spectral curves of all the pixels, but it is also possible to normalize spectral curves of required pixels on a case-by-case basis while performing the smoothing processing.

Further, in this system, the operation program of the CPU 23 is previously stored in the hard disk drive 26, but part or all of the program may be installed into the computer 20 from outside via the Internet, a storage medium, or the like.

Furthermore, in this system, each processing is executed by the computer 20, but part or all of the operations of the computer 20 may be executed by a device (control/image processing device) dedicated to the main body of the microscope 10.

Moreover, the main body of the microscope 10 of this system uses the multichannel light detector 19 to detect respective wavelength components of incident light, but instead of the multichannel light detector 19, a combination of one-channel light detector and a movable mask, a combination of plural one-channel light detectors and plural filters, or the like may be used. Note, however, that the use of the multichannel light detector 19 is advantageous in that space can be saved.

Further, the main body of the microscope 10 of this system is a fluorescent microscope which detects fluorescence generated on the sample 15, but may be a microscope which detects transmitted light or reflected light of light illuminating the sample 15. In this case, instead of the dichroic mirror 12, a beam splitter is used.

Furthermore, the main body of the microscope 10 of this system is a confocal microscope which confocally detects light from the sample 15, but the function of this confocal detection may be omitted. In this case, the pinhole mask 17 becomes unnecessary.

Additionally, the main body of the microscope 10 of this system is a scanning microscope which optically scans the sample 15, but may be a non-scanning microscope. In this case, the optical scanner 13 becomes unnecessary.

Namely, the present invention can be applied to various devices which perform spectral imaging.

The many features and advantages of the invention are apparent from the foregoing description. It is to be understood that the invention is not limited to the described embodiments, which are intended to be illustrative and not limiting. As will readily occur to those skilled in the art, numerous changes and modifications are possible in keeping with the principles and spirit of the invention, the scope of which is defined in the appended claims.

The invention claimed is:

1. A spectral image processing method of performing processing on a spectral image of a specimen, comprising:
    a step of normalizing spectra (=spectral brightness curves) of respective pixels constituting said spectral image such that their brightness levels become equal;
    a step of smoothing said normalized spectra in spatial directions of said respective pixels; and
    a step of denormalizing the smoothed spectra by multiplying them by respective brightness levels of corresponding pixels or values corresponding to the respective brightness levels.

2. The spectral image processing method according to claim 1, wherein
    said normalizing is performed such that brightness integral values of said spectra become equal, and
    said denormalizing is performed such that the brightness integral values of said spectra return to their respective values before said normalization.

3. The spectral image processing method according to claim 1, wherein
    said normalizing is performed such that brightness maximum values of said spectra become equal, and
    said denormalizing is performed such that the brightness maximum values of said spectra return to their respective values before said normalization.

4. The spectral image processing method according to claim 2, further comprising:
    an unmixing step of separating and finding respective contributions of plural materials contained in said specimen to said spectral image based on emission spectral information of said plural materials.

5. A non-transitory computer-readable storage medium storing a spectral image processing program which causes a computer to perform spectral image processing on a spectral image of a specimen by a method including:
    a step of normalizing spectra (=spectral brightness curves) of respective pixels constituting said spectral image such that their brightness levels become equal;
    a step of smoothing said normalized spectra in spatial directions of said respective pixels; and
    a step of denormalizing the smoothed spectra by multiplying them by respective brightness levels of corresponding pixels or values corresponding to the respective brightness levels.

6. A spectral imaging system, comprising:
    a spectral imaging unit which acquires a spectral image of a specimen; and
    a spectral image processing unit which imports said acquired spectral image and executes spectral image processing of the acquired spectral image, including:
        a step of normalizing spectra (=spectral brightness curves) of respective pixels constituting said spectral image such that their brightness levels become equal;
        a step of smoothing said normalized spectra in spatial directions of said respective pixels; and
        a step of denormalizing the smoothed spectra by multiplying them by respective brightness levels of corresponding pixels or values corresponding to the respective brightness levels.

7. The spectral image processing method according to claim 3, further comprising:
    an unmixing step of separating and finding respective contributions of plural materials contained in said specimen to said spectral image based on emission spectral information of said plural materials.

8. The non-transitory computer-readable storage medium according to claim 5, wherein the spectral image processing program causes the computer to perform said normalizing such that brightness integral values of said spectra become equal, and to perform said denormalizing such that the brightness integral values of said spectra return to their respective values before said normalization.

9. The non-transitory computer-readable storage medium according to claim 5, wherein the spectral image processing program causes the computer to perform said normalization such that brightness maximum values of said spectra become equal, and to perform said denormalizing such that the brightness maximum values of said spectra return to their respective values before said normalization.

10. The non-transitory computer-readable storage medium according to claim 8, wherein the spectral image processing program causes the computer to perform said spectral image processing method so as to further include:
    an unmixing step of separating and finding respective contributions of plural materials contained in said specimen to said spectral image based on emission spectral information of said plural materials.

11. The non-transitory computer-readable storage medium according to claim 9, wherein the spectral image processing program causes the computer to perform said spectral image processing method so as to further include:
    an unmixing step of separating and finding respective contributions of plural materials contained in said specimen to said spectral image based on emission spectral information of said plural materials.

12. The spectral imaging system according to claim 6, wherein
    said normalizing is performed such that brightness integral values of said spectra become equal, and
    said denormalizing is performed such that the brightness integral values of said spectra return to their respective values before said normalization.

13. The spectral imaging system according to claim 6, wherein
    said normalizing is performed such that brightness maximum values of said spectra become equal, and
    said denormalizing is performed such that the brightness maximum values of said spectra return to their respective values before said normalization.

14. The spectral imaging system according to claim 12, wherein said spectral image processing future includes:
    an unmixing step of separating and finding respective contributions of plural materials contained in said specimen to said spectral image based on emission spectral information of said plural materials.

15. The spectral imaging system according to claim 13, wherein said image processing further includes:

an unmixing step of separating and finding respective contributions of plural materials contained in said specimen to said spectral image based on emission spectral information of said plural materials.

* * * * *

UNITED STATES PATENT AND TRADEMARK OFFICE
CERTIFICATE OF CORRECTION

PATENT NO. : 8,055,035 B2
APPLICATION NO. : 11/913281
DATED : November 8, 2011
INVENTOR(S) : Okugawa et al.

Page 1 of 1

It is certified that error appears in the above-identified patent and that said Letters Patent is hereby corrected as shown below:

On the Title Page:

In item (75), the residence of the second inventor should read -- Ageo (JP) --.

Signed and Sealed this
Tenth Day of April, 2012

David J. Kappos
*Director of the United States Patent and Trademark Office*